United States Patent [19]

Hofer et al.

[11] 4,075,163

[45] Feb. 21, 1978

[54] BENZENE PHOSPHONOUS ACID COMPOUNDS, THEIR PRODUCTION AND USE AS STABILIZERS FOR ORGANIC MATERIALS

[75] Inventors: Kurt Hofer, Muenchenstein; Guenther Tscheulin, Frick, both of Switzerland

[73] Assignee: Sandoz Ltd., Basel, Switzerland

[21] Appl. No.: 668,598

[22] Filed: Mar. 19, 1976

Related U.S. Application Data

[62] Division of Ser. No. 463,867, April 25, 1974, Pat. No. 3,962,175, which is a division of Ser. No. 191,079, Oct. 20, 1971, Pat. No. 3,825,629.

[30] Foreign Application Priority Data

Oct. 22, 1970 Switzerland .................. 15605/70
June 30, 1971 Switzerland .................. 9597/71

[51] Int. Cl.² .................. C08K 5/50; C08K 5/53
[52] U.S. Cl. .................. 260/45.7 P; 106/177; 260/45.7 PS; 260/45.95 G; 260/932; 260/962
[58] Field of Search .................. 260/45.7 P, 45.7 PS; 106/177

[56] References Cited

U.S. PATENT DOCUMENTS

| | | | |
|---|---|---|---|
| 2,510,777 | 6/1950 | Gray | 260/45.7 P |
| 2,553,643 | 5/1951 | Ellerhorst, Jr. | 260/45.7 P |
| 2,606,169 | 8/1952 | Roney | 260/45.7 P |
| 3,050,499 | 8/1962 | Gordon et al. | 260/45.7 P |
| 3,061,583 | 10/1962 | Huhn et al. | 260/45.7 P |
| 3,231,531 | 1/1966 | Buckley et al. | 260/45.7 PH |
| 3,236,803 | 2/1966 | Huhn et al. | 260/45.7 P |
| 3,493,538 | 2/1970 | Salyer et al. | 260/45.7 P |
| 3,496,128 | 2/1970 | Casey et al. | 260/45.7 PS |
| 3,676,393 | 7/1972 | Piirma | 260/45.7 PS |
| 3,978,020 | 8/1976 | Liberti | 260/45.7 P |

OTHER PUBLICATIONS

Gefter, "Organophosphorus Monomers and Polymers", 1962, pp. XII and XIII.

*Primary Examiner*—Donald E. Czaja
*Assistant Examiner*—R. A. White
*Attorney, Agent, or Firm*—Gerald D. Sharkin; Richard E. Vila; Thomas C. Doyle

[57] ABSTRACT

The purpose of the invention are new benzene phosphonous acid compounds in which two to four benzene nuclei are bound together and which contain one to three phosphorus atoms. The new compounds are free acids, their salts with inorganic cations, their esters, thioesters or amides. The invention concerns also the manufacture of these benzene phosphonous acid compounds and their use for the stabilization of organic materials.

13 Claims, No Drawings

BENZENE PHOSPHONOUS ACID COMPOUNDS, THEIR PRODUCTION AND USE AS STABILIZERS FOR ORGANIC MATERIALS

This application is a division of our copending application Ser. No. 463,867 filed Apr. 25, 1974, now U.S. Pat. No. 3,962,175 which in turn is a division of our application Ser. No. 191,079, filed Oct. 20, 1971 and now U.S. Pat. No. 3,825,629.

The present invention concerns new benzene phosphonous acid compounds in which two to four benzene nuclei are bound together and which contain one to three phosphorus atoms. The new compounds are free acids, their salts with inorganic cations and their esters, thioesters and amides. The invention concerns especially the use of these benzene phosphonous acid compounds for the stabilization of organic materials. The new benzene phsophonous acid compounds of formula

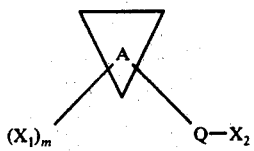
(I)

wherein
  $m$ is 1 or 2, ⟨A⟩ is unsubstituted or substituted diphenyl or terphenyl,
  Q is a single bond or an unsubstituted or substituted phenylene radical, $X_1$ is a radical of formula

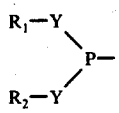
(II)

and
  $X_2$ is hydrogen or a radical of formula

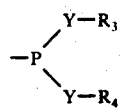
(IIa)

$R_1$, $R_2$, $R_3$ and $R_4$ are, independently, hydrogen or unsubstituted or a substituted hydrocarbon radical, containing up to 16 carbon atoms,
Y is oxygen, sulfur or a radical of formula

(III)

and
  Z, either bound to R, together with N-atom, forms a hetero cyclic ring or is the same as $R_1$, $R_2$, $R_3$ or $R_4$, are produced by the reaction of a compound of formula

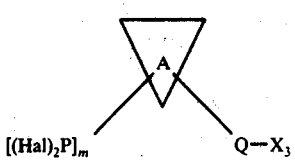
(IV)

wherein
  Hal is halogen and $X_3$ is hydrogen or a radical of formula

(V)

with so many mols per mol of the compound of formula (IV) of a compound of formula

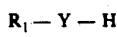
(VI)

or of a mixture of 2, 3 or 4 compounds of formulae $R_1 - Y - H$, $R_2 - Y - H$, $R_3 - Y - H$ and $R_4 - Y - H$, as Hal-radicals are present in the compound of formula (IV).

The starting materials of formula (IV) are new. They are produced from unsubstituted or substituted aromatic hydrocarbons, which are composed of 2, 3 or 4 benzene nuclei, bound together by single bonds. Examples for such hydrocarbons are: Diphenyl, o-, m- and p-terphenyl, m - quaterphenyl, p- quaterphenyl, 1,2,4-triphenyl-benzene and 1,3,5-triphenyl-benzene. From these starting materials the compounds of formula (IV) are produced by reaction with a phosphorus trihalide, preferably with phosphorus trichloride. This reaction can be performed at very high temperatures in the gaseous phase. To avoid side-reactions it is, generally, advantageous to effect the reaction under milder conditions, using catalysts. Friedel-Crafts-Catalysts are suitable, especially anhydrous aluminium chloride. One preferably works with an excess of phosphorus trichloride at its boiling temperature. Working up the reaction mixture, the aluminium chloride complex with the dichlorophosphine is first decomposed, for instance with phosphorus oxychloride or with pyridine. In principal these methods of manufacture are known. These and other analogous procedures for the production of compounds of formula (IV) are collectively described by K. Sasse in "Handbuch von Houben-Weyl, Methoden der Organischen Chemie, 4th Edition (1963), Vol. XII/1, organische Phosphorverbindungen", part 1, pages 302–318.

The starting materials, characterized by formula (VI), are: Water, hydrogen sulfide, ammonia, alcohols, phenols, mercaptans, thiophenols and organic primary and secondary amines.

The reaction of the starting materials of formulae (IV) and (VI) normally proceeds easily; to avoid side-reactions, it is often necessary to smooth the vehement reaction by cooling externally. Reacting with water, it is preferred to use it in excess, to cool and to add the halophosphine of formula (IV) so slowly, that the temperature does not rise too high due to the exothermic nature of the reaction. When the hydrolysis is effected in this way, there result colorless, powdery compounds, containing radicals of the following structure:

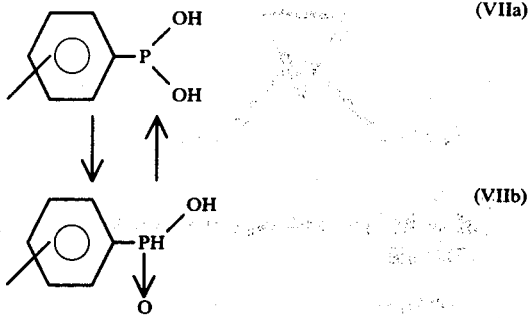

These derivatives of benzene phosphonous acid have acid properties and, by treating with inorganic bases or with salts containing inorganic cations, are converted to their corresponding salts. Examples for such inorganic reagents are: Calcium hydroxide, zinc-oxide, sodium carbonate, potassium hydrogen carbonate, aluminium acetate, barium chloride, nickel acetate and zinc chloride.

The hydrolysis of halophosphines of formula (IV) and the transformation of the hydrolysis products, which contain radicals of the above formulae (VIIa) or (VIIb) into their salts, may also be performed in a one step process. For this purpose, as described above, the water used for the hydrolysis is added in excess in advance, together with the desired inorganic reagent, followed with the halophosphine of formula (IV), which is slowly added by stirring. Moisture is carefully excluded if, instead of water, other compounds of formula (VI) are to be reacted. Generally phenols react smoothly if heated for instance to 100°–150° C, whereby the hydrogen halide splits off.

Acid binding agents, such as pyridine or trialkylamines can be added to bind the split off hydrogen halide.

This method is preferred if alcohols are reacted. If the compounds of formula (IV) are reacted with organic amines or with ammonia, these are used in excess, which serves as a binding agent for the hydrogen halide split off.

The described reactions are analogous processes, which are generally known. A respective collective summary has been published in the afore-mentioned book by K. Sasse (compare p.318 ff.).

Substituents in the polyphenyl radical represented by the symbol  [formulae (I) and (IV)], in the phenylene radical Q and also as radicals R [formulae (II) and (VI)] and Z[formula (III)] are alkyl- and cycloalkyl groups. Examples of such substituents are: methyl, ethyl, propyl, butyl, isobutyl, amyl, 2,2-dimethylpropyl, octyl, dodecyl, isopropyl, tert.-butyl, 2,6,8-trimethyl-4-nonyl, 2-ethyl-hexyl, 2,4,6,8-tetramethylnonyl and cyclododecyl.

The preferred polyphenyl radicals and the phenylene radical Q are unsubstituted; they may be substituted by halogen, especially by chlorine and bromine or by alkoxy radicals such as methoxy, ethoxy, propoxy, isopropoxy, butoxy, hexloxy, dodecyloxy and 2-ethylhexyloxy.

Besides the abovementioned hydrocarbon radicals which R and Z can signify, the latter can also signify aryl radicals, which as well as the alkyl radicals, may be substituted. Examples are the following substituents: Phenyl, 2-, 3- or 4-methylphenyl, dimethylphenyl (mixture of isomers), p-tert.butylphenyl, 2-methoxyphenyl, 3-chlorophenyl and dichlorophenyl (mixture of isomers), 2-methoxyethyl, 2-methoxypropyl, 2-phenoxyethyl, 2-(2'-phenoxyethoxy)-ethoxy, 2-cresoxyethyl, benzyl, 4-chlorobenzyl, 2,4-dichlorobenzyl, 2-chloroethyl and substituents of formula $$CH_3(OCH_2CH_2)_p-\qquad\qquad(VIII)$$

wherein p mens one of the numbers 2 to 12.

Examples for those cases, in which the radicals Z and R are connected with each other and form, together with the N-atom [formula (III)] a heterocyclic ring, are pyrrolidino, piperidino, hexamethylenimino and morpholino.

The invention also concerns the new compounds of formula (I) and their use as stabilizers.

For this purpose the new compounds are either incorporated in the product or material sensitive to light, oxygen and heat, or applied to its surface to form a protective film. By their stabilizing effect they protect these sensitive substances from degradation. They have a wide range of application in the processing of plastics; to name some examples, they can be employed as stabilizers for cellulose acetate, cellulose proprionate, cellulose acetobutyrate, polyethylene, polypropylene, polyvinyl chloride, polyvinyl chloride-acetate, polyamides, polystyrene, ethyl cellulose, cellulose nitrate, polyvinyl alcohol, silicon rubber, melamine-formaldehyde and urea-formaldehyde resins, allyl casting resins, polymethylmethacrylate, polyesters and polyacrylonitrile. The compounds can also be used to protect natural products such as rubber, cellulose, wool and silk from degradation.

The products or materials for protection may be present in the form of sheet or film, panels, tubing, rods, tapes, coatings, fibres, granules, powders or other solid forms, or as solutions, emulsions or dispersions. The stabilizers are incorporated in, or applied to these materials by the known methods. One of the main methods of application is intimate mixing of the stabilizer and the plastic material, e.g. polypropylene granules, in a kneading or other suitable machine and extrusion moulding of the mixture. This technique ensures homogeneous blending, which is important for effective protection. Extrusion moulding is employed to produce a variety of products, including films, tubing and filaments. The latter can be converted into woven fabrics.

If polypropylene, for instance, is to be processed as woven fabric the stabilizer is normally mixed with it prior to extrusion as filament yarn. However, these new stabilizers can be applied with equally good effect to textile yarns and fabrics, for example from an aqueous bath containing the compound of formula (I) in superfine dispersion. Textiles of polyester and cellulose acetate fibres are suitable for this exhaust method of application.

The plastics need not necessarily be polymerized when the new compounds are added. The latter can be blended with the monomers or prepolymers prior to the condensation or other polymerization reaction yielding the final polymer.

Besides their use for the stabilization of clear films, plastics and the like, the new stabilizers are suitable for application in or on opaque, semi-opaque and translucent materials having a surface which is subject to degradation by light, oxygen and heat. Examples of such materials are foamed plastics, opaque films and sheeting, opaque papers, transparent and opaque pigmented plastics, fluorescent pigments and automobile and furniture polishes, creams, lotions and similar products, which latter group of products may be opaque, clear or translucent.

Benzene phosphonous acid esters and their stabilizing effect are known from literature. Comparing these compounds, for instance with those described in the Belgian Pat. No. 724,802, the new compounds of formula (I) have essential advantages. They are less fugitive, have less inclination for migration and are more soluble in many materials to be protected. Moreover the connection of at least two benzene nuclei in the new compounds of formula (I) has the effect, that they absorb ultra violet rays. They therefore do not only protect against heat and oxygen but also against the decomposition of sunlight. comparable phosphorus compounds are not known to have such combined protective effect. In spite of this polyvalent effect it is in many cases advantageous to mix the new stabilizers with other types of light absorbers or of stabilizers.

Such mixtures of agents often have a synergistic effect and protect the treated materials at the same time in a particularly high degree against ultra violet light, heat and oxidative disintegration.

As explained above the new compounds of formula (I) can be used as stabilizers for various organic materials. Depending the kind and number of the substituents the compounds of formula (I) are more or less suited for the protection of a certain organic material. The following relationships between the chemical constitution of the compounds of formula (I) and plastics, which have to be protected, have for instance been observed: To protect polypropylene, such agents are especially suited, which contain one or several aliphatic or cycloaliphatic radicals which contain at least 6, preferably 8 to 20 carbon atoms. To protect polyvinylchloride such agents are especially suited, whose substituents R contain aryl radicals, which may be substituted with lower alkyl radicals or with chloro atoms. For the protection of polyesters and of polyamides those agents are especially suited which contain several ether groups in the substituents R.

The present invention concerns also the materials which contain compounds of formula (I) for stabilization. As shown above in some examples, the incorporation of the new compounds into the materials that need protection can be effected at any stage of processing according to known methods, whereby the amount of added protective agents may vary within wide limits, for instance between 0.01 and 5%, preferably between 0.05 to 1%, related to the materials that need protection.

In the following examples F means melting point; Kp boiling point; λ wavelength, λ max the wavelength of maximum light absorption in nanometer units; parts and per cents are by weight and temperatures in degrees centigrades.

EXAMPLES FOR THE PRODUCTION OF THE INTERMEDIATE PRODUCTS OF FORMULA (IV)

a. In the absence of moisture a solution of 46.2 parts of diphenyl, 165 parts of phosphorus trichloride, and 44.8 parts of AlCl₃ is heated under reflux during the course of 3 hours; 53.5 parts of phosphorus oxychloride are subsequently added and the mixture is stirred for a further 15 minutes. After cooling to 0° the AlCl₃POCl₃ complex, precipitated in the form of granules, is filtered off, is washed thoroughly with chlorobenzene, and the filtrate is evaporated in a vacuum. As residue 65 parts (85% of theory) of 4-diphenyl-dichlorophosphine of formula

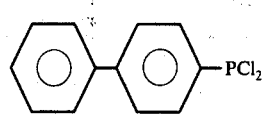

(IX)

are obtained in the form of a red, light oil of a pungent smell.

b. Working up is effected as described under (a), but in place of 44.8 parts of AlCl₃, 106 parts are used, and in place of 53.5 parts of phosphorus oxychloride, 122.6 parts are used. Thus, 85.2 parts of 4,4'-diphenyl-bis-(dichlorophosphine) of formula

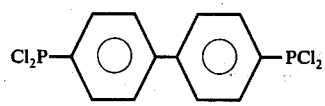

(X)

are obtained in the form of a red, light oil of a pungent smell.

c. In the absence of moisture a solution of 34.5 parts of p-terphenyl, 330 parts of phosphorus trichloride, and 52 parts of aluminium chloride are heated under reflux during the course of 5 hours; 61.3 parts of phosphorus oxychloride are subsequently added and the mixture is stirred for a further 15 minutes, is cooled to 0°, the resulting Al-complex is filtered off, is washed with phosphorus trichloride, and the filtrate is evaporated in a vacuum.

As residue 29 parts of 4,4''-(p-terphenyl)-bis-(dichlorophosphine) of formula

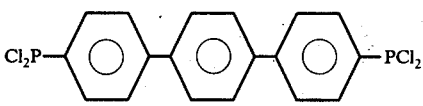

(XI)

are obtained in the form of light yellow crystals.

Examples for the end-products of formula (I) are listed in the following table 1 where the melting points of crystalline compounds are indicated in column F. These compounds melt at a temperature considerably higher than room temperature. The other indicated compounds are specified in column F as 'oil'. λmax. means the maximum of light absorption which is expressed by nanometer (nm) units. The constitution formulae indicated in table 1 are confirmed by elementary analyses.

Table 1

Constitution of the compounds of general formula

| Ex. No. | R₁ | R₂ | F | λmax. (nm) |
|---|---|---|---|---|
| 1 | —O—C₄H₉ | R₁=R₂ | oil | 252 |
| 2 | —O—C₈H₁₇(iso) | R₁=R₂ | oil | 250 |
| 3 | —O—⟨○⟩—C₉H₁₉ | R₁=R₂ | oil | 253 |
| 4 | —O—⟨○⟩—C₉H₁₉ | —O—C₄H₉ | oil | 254 |

Table 1-continued

| # | | | | |
|---|---|---|---|---|
| 5 | —O—⟨O⟩—C₉H₁₉ | —O—C₈H₁₇(iso) | oil | 253 |
| 6 | —S—C₁₂H₂₅ | R₁=R₂ | 42–43° | 270 |
| 7 | —S—⟨O⟩—+ * | R₁=R₂* | 110–111° | 255 |
| 8 | —N⟨O⟩ (morpholino) | R₁=R₂ | 168–169° | 263 |

$$R_1\!\!\diagdown\!\!P\text{—}\langle O\rangle\text{—}\langle O\rangle\text{—}P\!\!\diagup\!\!R_1$$
$$R_1\diagup\qquad\qquad\qquad\diagdown R_2$$

| # | | | | |
|---|---|---|---|---|
| 9 | —O—C₄H₉ | R₁=R₂ | oil | 260 |
| 10 | —O—C₈H₁₇(iso) | R₁=R₂ | oil | 259 |
| 11 | —O—C₁₃H₂₇ | R₁=R₂ | oil | 259 |
| 12 | —O—⟨O⟩—+ * | R₁=R₂* | 94–96° | 273 |
| 13 | —O—⟨O⟩—C₉H₁₉ | R₁=R₂ | oil | 265 |
| 14 | —O—⟨O⟩—C₉H₁₉ | —O—C₈H₁₇ | oil | 268 |
| 15 | —S—C₁₂H₂₅ | R₁=R₂ | 54–56° | 300 |
| 16 | —S—⟨O⟩—+ * | R₁=R₂* | 184–186° | 250 |
| 17 | —N(C₄H₉)₂ | R₁=R₂ | oil | 261 |
| 18 | —O—⟨O⟩—C₉H₁₉ | —O—C₈H₁₇(iso) | oil | 271 |
| 19 | —O—⟨O⟩—C₉H₁₉ | —O—C₄H₉ | oil | 262 |
| 20 | —O—⟨O⟩—+ | —O—C₄H₉ | oil | 264 |
| 21 | —S—C₁₂H₂₅ | —O—C₈H₁₇(iso) | oil | 264 |

$$R_1\!\!\diagdown\!\!P\text{—}\langle O\rangle\text{—}\langle O\rangle\text{—}\langle O\rangle\text{—}P\!\!\diagup\!\!R_1$$
$$R_1\diagup\qquad\qquad\qquad\qquad\diagdown R_2$$

| # | | | | |
|---|---|---|---|---|
| 22 | —O—C₈H₁₇ | R₁=R₂ | oil | 292 |
| 23 | —O—⟨O⟩—+ * | R₁=R₂* | 199–199.5° | 298 |
| 24 | —O—⟨O⟩—C₉H₁₉ | R₁=R₂ | oil | 292 |
| 25 | —O—⟨O⟩—C₉H₁₉ | —O—C₄H₉ | oil | 292 |
| 26 | —S—C₁₂H₂₅ | R₁=R₂ | 63–65° | 308 |
| 27 | —S—⟨O⟩—+ * | R₁=R₂* | 187–189° | 310 |
| 28 | —N(C₄H₉)₂ | R₁=R₂ | oil | 296 |

* The symbols + signify the tertiary butyl radical.

EXAMPLES FOR THE PRODUCTION OF END-PRODUCTS OF FORMULA (I)

The Examples are numbered in the same way as the corresponding compounds of the above table 1.

EXAMPLE 7

In the absence of moisture a solution of 43.5 parts of 4-diphenyldichlorophosphine [Example a), formula (IX)] in 100 parts of toluene is added at 0°–5° to 56.8 parts of 4-tert.butylthiophenol and 35 parts of triethylamine in 200 parts of toluene; the mixture is allowed to react over night at 40°, the precipitated triethyl ammonium chloride is filtered off, the filtrate is evaporated in a vacuum, and the oily residue is purified by crystallization from methanol-ether. Constitution formula and characterization of this compound and the compounds of the production Examples cited below are indicated in the above table 1.

EXAMPLE 9

In the absence of moisture a solution of 28.35 parts of 4,4'-diphenyl-pis-(dichlorophosphine) [Example b), formula (X)] in 100 parts of chlorobenzene is added at 0°–5° to 23.6 parts of n-butanol and 32 parts of triethylamine in 300 parts of chlorobenzene; the mixture is allowed to react over night at 40°, the precipitated salt is filtered off, the filtrate is evaporated in a vacuum, and a light yellow oil is obtained.

EXAMPLE 13

A solution of 47.5 parts of 4.4'-diphenyl-bis-(dichlorophosphine) in 100 parts of toluene is added at 0°–5° to 117.5 parts of 4-nonylphenol and 55 parts of triethylamine in 400 parts of toluene; the mixture is allowed to react over night at 50°–60°, the precipitated triethyl ammonium chloride is filtered off, the filtrate is evaporated in a vacuum, and thus, a yellow viscous residue is obtained.

The same compound is also obtained by mixing the starting materials without triethylamine and without toluene and gradually heating to 140°–160°, while carbon dioxide is passed through the mixture, until the evolution of hydrogen chloride ceases.

EXAMPLE 15

A solution of 20.0 parts of 4,4'-diphenyl-bis-(dichlorophosphine) in 100 parts of toluene is added at 0°–5° to 45.4 parts of dodecyl mercaptan and 22.8 parts of triethylamine in 200 parts of toluene; the mixture is then allowed to react over night at 40°, the precipitated triethyl ammonium chloride is filtered off, the filtrate is evaporated in a vacuum, and the residue is crystallized from ether.

EXAMPLE 27

A solution of 31.0 parts of 4,4'''-(p-terphenyl)-bis-(dichlorophosphine), Example c), formula (XI), is added at 0°–5° to 48.1 parts of 4-tert.butyl thiophenol and 30.1 parts of triethylamine in 300 parts of toluene; the mixture is allowed to react over night at 40°, the precipitated triethyl ammonium chloride is filtered off, the filtrate is evaporated in a vacuum, and the residue is crystallized from benzene-methanol.

In place of 30.1 parts of triethylamine, 24 parts of anhydrous pyridine may also be used as acid-binding agent.

In Examples 4, 5, 14, 18, 19, 20, 21, and 25 of table 1 there are mentioned esters of phosphorous acids which contain in the same molecule radicals derived from different alcohols, phenols or mercaptans. The production thereof is effected in analogous manner as described in the above production Examples by reacting the chlorophosphines with a mixture of the appropriate alcohol, phenol or mercaptan reagents. Thus, mixtures of esters are always obtained; aside from the main constituents which are characterized by the formulae of Examples 4, 5, 14, 18, 19, 20, 21, and 25 these mixtures also contain other esters, wherein the equivalent ratio of the radicals is shifted.

The following Examples relate to end-products which are obtained by hydrolysis of 4,4'-diphenyl-bis-(dichlorophosphine) of formula (X), partly as free phosphonous acids, and partly in the form of the salts with inorganic cations.

EXAMPLE 29

80 parts of 4,4'-diphenyl-bis-(dichlorophosphine) of formula (X), produced as described in Example b), are diluted with 20 parts of chlorobenzene and slowly added to 300 parts of water while stirring well, and the temperature is kept at 0°-5° by external cooling. The reaction is completed at 20° after 18 hours. The thin colourless precipitate is filtered off and is dried at 90° in a vacuum. The obtained crude product is appropriate for the use as stabilizer. It mainly consists of the compound of formula

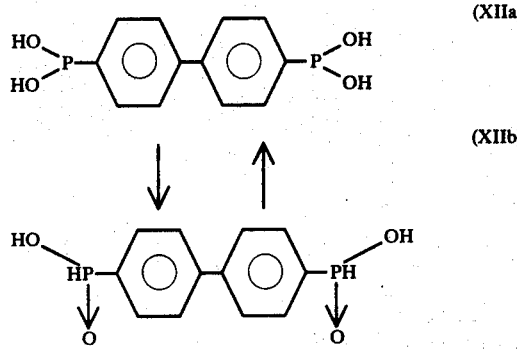

(XIIa)

(XIIb)

and impurities which probably consist of anhydrides of the acid of formula (XII). Other impurities furthermore contain chlorine, as a small part of the chlorine atoms in the starting product of formula (X) has escaped from hydrolysis by coating with the insoluble precipitate.

EXAMPLE 30

The process described in Example 29 may be simplified by hot isolating or purifying the intermediate product of formula (X) (precipitation of the aluminium chloride by phosphorus oxychloride).

46,2 parts of diphenyl, 106 parts of aluminium chloride, and 165 parts of phosphorus trichloride are heated under reflux during the course of 2 hours; the excess of phosphorus trichloride is subsequently removed by distillation and the viscous residue is taken up in 40 parts of chlorobenzene. Hydrolysis is then effected with 300 parts of water as described in Example 29. The obtained fine colourless powder contains 16.7% of phosphorus, 1.1% of chlorine, and 3.8% of aluminium.

EXAMPLE 31

The 4-diphenyl-dichlorophosphine of formula (IX) described in Example a) is hydrolized in accordance with the method described in Example 29; after the working up a colourless fine powder is obtained which mainly consists of the compound of the following formula

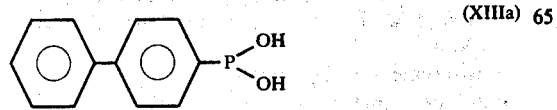

(XIIIa)

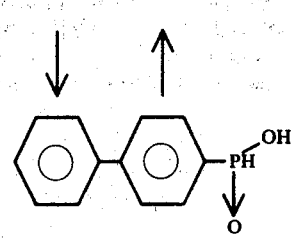

(XIIIb)

EXAMPLE 32

26 parts of the compound obtained in accordance with Example 29 are mixed by stirring with a solution of 21 parts of barium chloride in 100 parts of water and boiled under reflux during the course of 3 hours. After cooling to 5° the colourless precipitate is filtered, is washed with water and is dried at 90° in a vacuum. The resulting barium salt contains 18.9% of barium.

In annalogous manner the light green nickel salt (content of nickel is 6%) is obtained from 25 parts of nickel acetate and the colourless zinc salt (content of zinc is 4.1%) from 27 parts of chloride of zinc.

EXAMPLE 33

Proceeding in manner analogous to that described in Example 30 the resulting colourless powder is suspended in 400 parts of water while stirring; calcium oxide is gradually added at such an amount that after stirring at 80° for a longer period the pH value does not sink below 5°; the mixture is cooled to 5° and the precipitate is filtered. The resulting colourless slat contains 4.1% of calcium, 6.3% of aluminium, and 3.3% of chlorine.

EXAMPLES FOR THE USE OF THE END-PRODUCTS OF FORMULA (I)

A. Stabilization against oxidative degradation

A few of the compounds cited in the above Examples are tested in regard to their effect as stabilizers against oxygen as follows: 0.1% of a compound of formula (I) is homogeneously incorporated in polypropylene which contains 0.2% of 4,4'-methylene-bis-(2,6-di-tert-.butylphenol) as anti-oxidant agent. After displacing the air, the plastics in the form of thin small plates is then kept under oxygen in a closed system. Then it is heated to 190°, whereby an excess pressure of about 20 mm Hg develops. The oxidation of the plastics results in a decrease of pressure. The rate of this decrease of pressure is small if the effectiveness of the stabilizer or the mixture of the stabilizers is high. The test results are summarized in the following Table 2. The figures signify the time expressed in minutes which passes until the excess pressure decreases to zero.

Table 2

| Incorporated phosphorus compounds of formula (I) | |
|---|---|
| Example No. | minutes |
| — | 119 |
| 29 | 179 |
| 30 | 193 |
| 31 | 200 |
| 32 (Ba - salt) | 229 |
| 32 (Ni - salt) | 207 |
| 32 (Zn - salt) | 290 |
| 33 | 195 |

In a further series of tests 0.07% of 4,4'-methylene-bis-(2,6-di-tert.butylphenol) and 0.13% of dilaurylthiodipropionate were used for the fundamental stabilization of the polypropylene and for the rest checked comparatively as described above. The results are summarized in the following table 3.

compound of the above Table 1 it remains colourless after 4 days at 140°.

Formulae of representative benzene phosphonous acid compounds of the foregoing examples are as follows:

Example 3

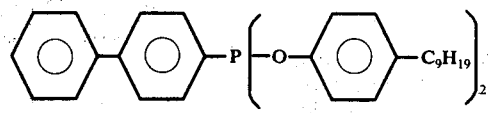

Example 16

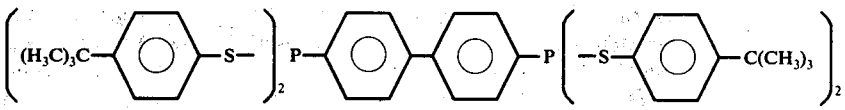

Example 19

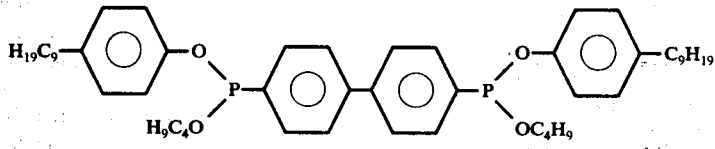

Example 26

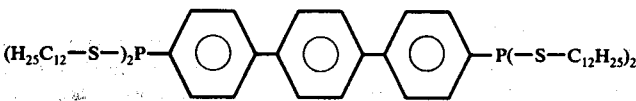

Example 31

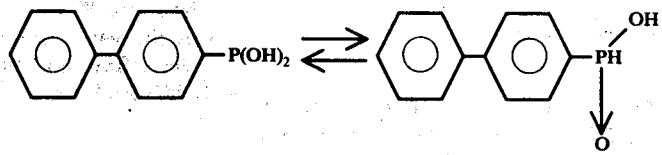

Table 3

| Incorporated phosphorus compounds of formula (I) | |
|---|---|
| Example No. | minutes |
| — | 48 |
| 3 | 96 |
| 5 | 61 |
| 6 | 102 |
| 9 | 78 |
| 10 | 84 |
| 12 | 105 |
| 13 | 165 |
| 14 | 81 |
| 15 | 105 |
| 18 | 102 |
| 19 | 177 |
| 20 | 98 |
| 21 | 96 |
| 26 | 89 |
| 27 | 60 |

B. Stabilization against brownish discoloration

While incorporating 0.2% of the stabilizer 2,2'-methylen-bis-(4-methyl-6-tert.butylphenol) in polypropylene at about 220° a brownish discoloration takes place. This discoloration may be avoided if 0.1% of a compound of formula (I) is incorporated at the same time.

In the ageing of small plates of polypropylene in a furnace at 140° a strong brownish discoloration takes place after only one day if the plastics only contains 0.2% of 2,2'-methylen-bis-(4-methyl-6-tert.butyl-phenol). If the plastics furthermore contains 0.1% of a

What is claimed is:

1. A composition stabilized against the effect of light, oxygen and/or heat which comprises an organic polymeric material which is sensitive to said effect and an effective amount of a stabilizing agent of the formula

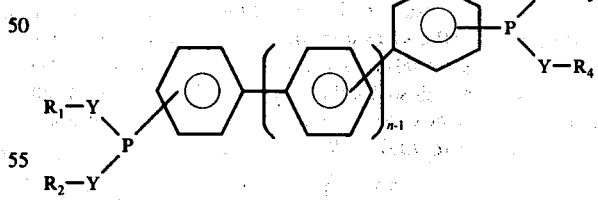

wherein each of
  $R_1$, $R_2$, $R_3$ and $R_4$, independently, is a hydrocarbon radical of up to 16 carbon atoms, selected from the group consisting of alkyl which is unsubstituted or substituted by methoxy, phenoxy, cresoxy or chloro, cycloalkyl, aryl which is unsubstituted or substituted by methoxy or chloro, alkylaryl and benzyl which is unsubstituted or substituted by chloro,
Y is oxygen or sulphur
$n$ is 1 or 2 and the polyphenylene moiety is unsubstituted or substituted by alkyl, cycloalkyl, chlorine, bromine or alkoxy.

2. A composition according to claim 1, wherein $n$ is 1.

3. A composition according to claim 1, wherein Y is oxygen.

4. A composition according to claim 1, wherein each of $R_1$, $R_2$, $R_3$ and $R_4$, if aryl, is phenyl and, if alkylaryl, is alkylphenyl.

5. A composition according to claim 3, wherein the stabilizing agent is of the formula

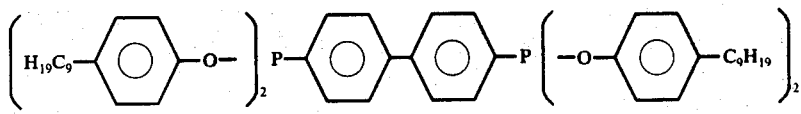

6. A composition according to claim 2, wherein the stabilizing agent is of the formula

7. A composition according to claim 3, wherein the stabilizing agent is of the formula

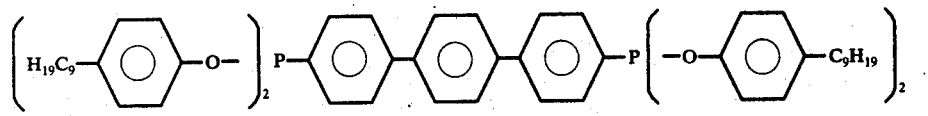

8. A composition according to claim 3, wherein the stabilizing agent is of the formula

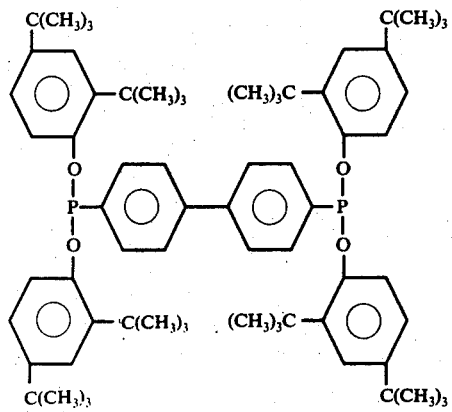

9. A composition according to claim 1, wherein the susceptible material comprises a plastics material.

10. A composition according to claim 9, wherein the plastics material is selected from cellulose acetate, cellulose proprionate, cellulose acetobutyrate, polyethylene, polypropylene, polyvinyl chloride, polyvinyl chloride-acetate, polyamides, polystyrene, ethyl cellulose, cellulose nitrate, polyvinyl alcohol, silicon rubber, melamine-formaldehyde and urea-formaldehyde resins, allyl cast resins, polymethylmethacrylate, polyesters and polyacrylonitrile.

11. A composition according to claim 1, which contains between 0.01 and 5% of the stabilizing agent, based on the weight of the susceptible material.

12. A composition according to claim 1 wherein $R_1$, $R_2$, $R_3$ and $R_4$ and the polyphenylene moiety are unsubstituted.

13. A composition according to claim 10 wherein the plastics material is polypropylene.

* * * * *